United States Patent [19]
Duffy et al.

[11] Patent Number: 5,146,651
[45] Date of Patent: Sep. 15, 1992

[54] PROCESS AND APPARATUS FOR TOW CROSS-SECTION MEASUREMENT AND CONTROL

[75] Inventors: Joseph J. Duffy, Newark; Jerry F. Potter, Seaford; Elwood A. Roth, Seaford; Kalika R. Samant, Seaford; Richard E. Thek, Seaford, all of Del.; Maurice C. Todd, Chadds Ford, Pa.

[73] Assignee: E. I. Du Pont de Nemours and Company, Wilmington, Del.

[21] Appl. No.: 631,432

[22] Filed: Dec. 21, 1990

[51] Int. Cl.⁵ .......................................... D01G 23/06
[52] U.S. Cl. .................................. 19/65 T; 19/65 A; 28/185; 28/282; 226/18
[58] Field of Search ............ 19/0.23, 65 T, 65 R, 19/65 A, 150, 157, 161.1, 296, 297, 300; 28/185, 187, 240, 242, 247, 248, 263, 282; 226/2, 15, 18-23

[56] References Cited

U.S. PATENT DOCUMENTS

| | | | |
|---|---|---|---|
| 2,920,176 | 1/1960 | Jorgensen | 28/282 X |
| 2,950,520 | 8/1960 | Sonnino | 19/0.23 X |
| 3,017,309 | 1/1962 | Crawford et al. | 28/282 X |
| 3,046,632 | 7/1962 | Tsutsumi | 28/282 X |
| 3,145,429 | 8/1964 | Resor | 19/157 |
| 3,204,295 | 9/1965 | Amos | 19/65 T |
| 3,231,958 | 2/1966 | Chadwick | 28/1 |
| 3,248,103 | 4/1966 | Tarbell | 270/52 |
| 3,270,937 | 6/1966 | Harrell | 19/65 T |
| 3,277,537 | 10/1966 | Roeder et al. | 19/161 |
| 3,282,768 | 11/1966 | Caines et al. | 28/263 X |
| 3,386,145 | 6/1968 | Harris | 28/282 X |
| 3,423,806 | 1/1969 | Dickins, III | 28/1 |
| 3,503,100 | 3/1970 | Glynn, III et al. | 28/282 X |
| 3,503,105 | 3/1970 | Sizemore | 28/282 X |
| 3,526,350 | 9/1970 | Tradewell et al. | 226/18 |
| 3,567,091 | 3/1971 | Woolard | 226/18 |
| 3,570,735 | 3/1971 | Kurz | 226/3 |
| 3,662,056 | 5/1972 | Ross | 19/65 T X |
| 4,646,387 | 3/1987 | Oswald et al. | 19/0.23 |
| 4,860,406 | 8/1989 | Staheli et al. | 19/105 |
| 4,974,301 | 12/1990 | Beerli et al. | 28/185 X |

FOREIGN PATENT DOCUMENTS

| | | |
|---|---|---|
| 47-32141 | 8/1972 | Japan . |
| 60-55607 | 12/1985 | Japan ........................ 19/300 |
| 0816778 | 7/1959 | United Kingdom . |
| 2023675 | 1/1980 | United Kingdom .............. 28/282 |

Primary Examiner—Werner H. Schroeder
Assistant Examiner—Ismael Izaguirre

[57] ABSTRACT

Controlling the cross-sectional characteristics of moving tow lines by providing monitors and positioning devices so as to improve stuffer box crimp uniformity. The mass distribution profile of a filamentary tow band is continuously measured as a function of the width of the band, and the information obtained is used to change the position of the band when a deviation from a predetermined value is noted. Positioning devices are used to carry out the movement or adjusting of the band in accordance with a signal so as to correct the deviation and present to a crimping apparatus, such as a stuffer box crimper, a band having a uniform mass distribution profile.

2 Claims, 12 Drawing Sheets

INDIVIDUAL BAND
WIDTHS DIFFERENT

CENTROID
DIFFERENCES

IMPROPER
STACKING

IMPROPER COMPOSITE
BAND WIDTH
(TOO WIDE)

OFF CRIMP AT EDGES,
BAND IN LIMITS
(OPERATOR VISUAL CHECK)

PROCESS AND APPARATUS FOR TOW CROSS-SECTION MEASUREMENT AND CONTROL

BACKGROUND OF THE INVENTION

1. FIELD OF THE INVENTION

This invention is concerned with the production of synthetic fibers. It is particularly concerned with that step in fiber production wherein a plurality of tow bands of drawn continuous filaments are guided to form a composite bundle array suitable for crimping in a stuffer box crimper.

2. DESCRIPTION OF THE RELATED ART

Various types of equipment have been used to converge and shape tow of fibers for stuffer box crimping. However, as production methods change and different products are processed on the same equipment, the apparatus used in production must be changed or adjusted. These changes are normally done manually by operators at the beginning of production runs and seldom are checked throughout the run. Typically the operators make visual checks of the crimp uniformity tow shape and edge position to determine the appropriate adjustments for the guides.

There is a problem with visual checks and edge measurements in that they do not account for variations in tow thickness between the edges, i.e. uneven tow mass distribution which results in non-uniform crimp.

Most synthetic staple fibers are given an appreciable amount of crimp to facilitate their conversion into spun yarn and, in the case of carpet fibers, to improve bulk and coverage to enhance apparent value of the final product. Most commonly, this crimp is established by passing a plurality of tow bands of drawn continuous filaments through a "stuffer box" type crimper as disclosed by U.S. Pat. No. 2,311,174 to Hitt. In that crimper device the bundle of continuous filaments is led into the nip of two rolls and forced into a restricting chamber against a movable gate.

Pressure applied to the gate by an air cylinder or spring causes the bundle to fold back upon itself and crimp is formed. The back pressure applied to the gate, the nip roll pressure, speed and denier loading of the crimper establish the crimp level and geometry (frequency and amplitude) of the crimp. The Hitt crimping device and most commercially available crimpers can handle relatively wide variations in bundle thickness uniformity. This can result in the crimpers producing a wide variation in across-the-band crimp variability without detection or upset. Since crimp loading on most commercial crimpers can be varied across a broad range of from 50,000 to 400,000 denier per inch of roll loading, considerable variability in tow geometry and crimp level can occur, especially at high denier loading without process upset or visual observation of change. If the tow band fed to the crimper is not uniform, it will not be evenly squeezed between the feed rolls of the crimper which results in non-uniform crimp both across and along the tow band. In extreme cases fiber damage can also occur from localized slippage or abrasion. Thick sections are gripped more positively and crimping force is more effectively transmitted to these sections resulting in higher crimp. Conversely, thinner sections transmit load less effectively which results in low crimp regions. After crimping, the tow should also have the crimped fibers uniformly intermeshed so the bundles hold together without splitting which impacts on downstream process uniformity such as cut length. Hence, the distribution of the tow fibers or filaments preparatory to crimping is an important step in the conversion process and it must be controlled to achieve good crimp uniformity.

When dynamic changes occur, they must be detected and immediate corrective action taken if product uniformity is to be controlled within the tight limits demanded for quality spun products. To achieve high quality in crimp uniformity, tow entering a crimper must be shaped and formed to provide as uniform a cross section as possible.

The prior art utilized any number of devices such as stacking bars or rolls, curved bars or rolls, and edge sensing and automatic centering devices to accomplish the guiding task. These devices used alone or in combination, are normally set at the beginning of production runs based on visual inspection or limited crimp measurements of the tow by the operator and changes are seldom attempted unless a process upset occurs. Where automatic operation was attempted, it was limited to centering the edges of the tow and controlling its width with no concern for the actual tow cross-section characteristics or alignment required for across band crimp uniformity.

SUMMARY OF THE INVENTION

The invention is a process and apparatus to improve stuffer box crimp uniformity by monitoring and controlling the cross-section characteristics of moving tow bands as they are processed through a draw machine and enter a stuffing box crimping device. The apparatus includes one or more indexing tow band thickness or mass profile monitoring devices, a series of remotely operated motorized guides with position detection capability strategically located throughout the draw crimping process, an advisory or feedback control system capable of establishing and maintaining optimum guiding adjustments required to obtain a predetermined tow profile for crimp uniformity and a controller/operator interface which converts the information into a visual display of the tow cross-section profile for both operator interaction and diagnostic purposes.

The monitoring device mounted on a variable speed indexing mechanism with a position sensing capability can either traverse across the running tow lines or be parked in a fixed location to look at along end uniformity. The primary purpose of the monitors are to provide a continuous input of dynamic tow band cross-section characteristics for real time process control. This allows the operator optional advisory control system (ACS) or closed loop controller (CLC) to make fine adjustments to the guiding system to better position tows to insure a predetermined cross section is fed into the crimper.

DESCRIPTION OF THE PREFERRED EMBODIMENTS

Figure 1A:
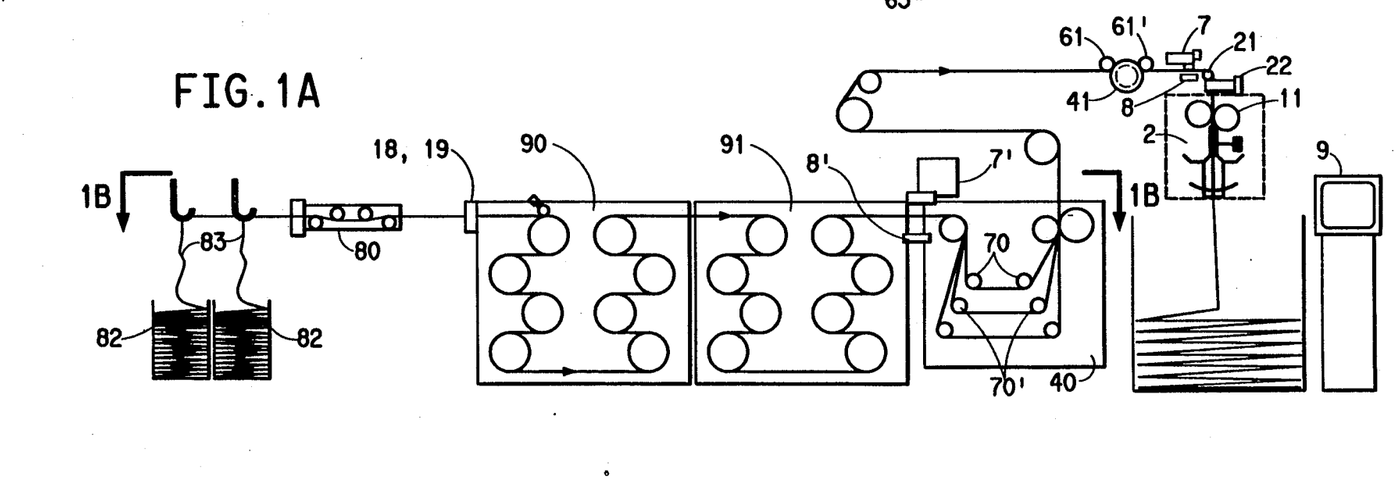
Figs. 1A and 1B are elevation and partial plan view, respectively, of a tow processing line including a tow mass distribution system of the invention.
Figure 1B:
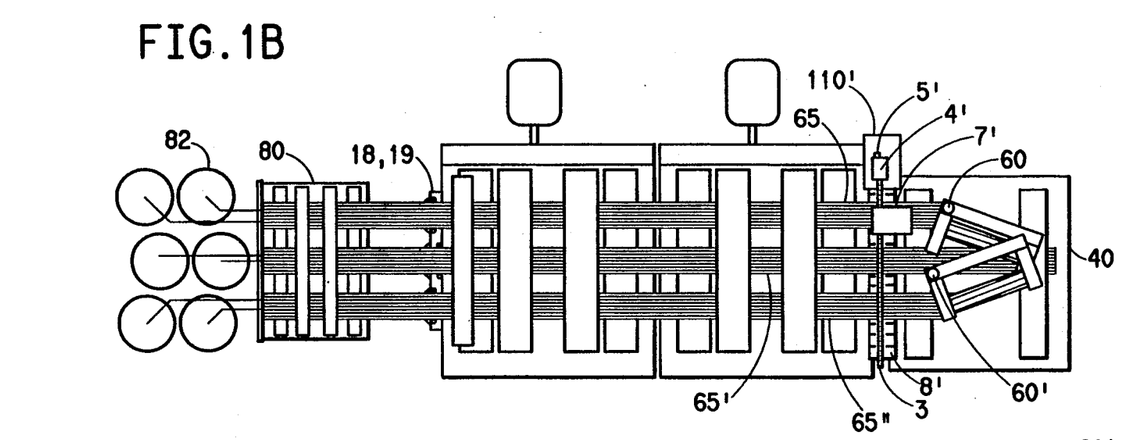

In a staple draw process shown in Figs. 1A and 1B, undrawn yarn 83 is taken from large storage containers 82 and passed through a pretensioning device 80 consisting of a series of bars where tows are flattened and preliminary position is established. A number of tows are combined and passed through a band width control device 19, then fed into a draw machine feed module 90 which in turn feeds a draw module 91 which is normally run at 3.5 to 4.0 times the speed of the feed module. Individual drawn tow lines are leveled during drawing due to tension and, if properly guided at the infeed, their relative position on exiting the draw line is fixed. These drawn tow lines pass from the draw module into a commercial stacking device 40 which contains a series of pivoting rolls 70 where bands are stacked to form one composite band of width approximately equal to that of the crimper rolls 11. Additional shaping and width control is accomplished at rolls 41, 61 and 61'. Before feeding into the crimper 2, edge rollers 22 are used for final shaping and guiding.

One or more cross section characteristic monitors 7 and/or 7' are used to provide input for guiding adjustment by the operator or an automatic control system. Change of direction guide 21 is a flat roll having the same width as the crimper rolls and precision aligned with the exit roll of the draw machine and crimper rolls to feed the shaped tow into the crimper without disturbing its shape; its position is fixed.

Figure 2A:
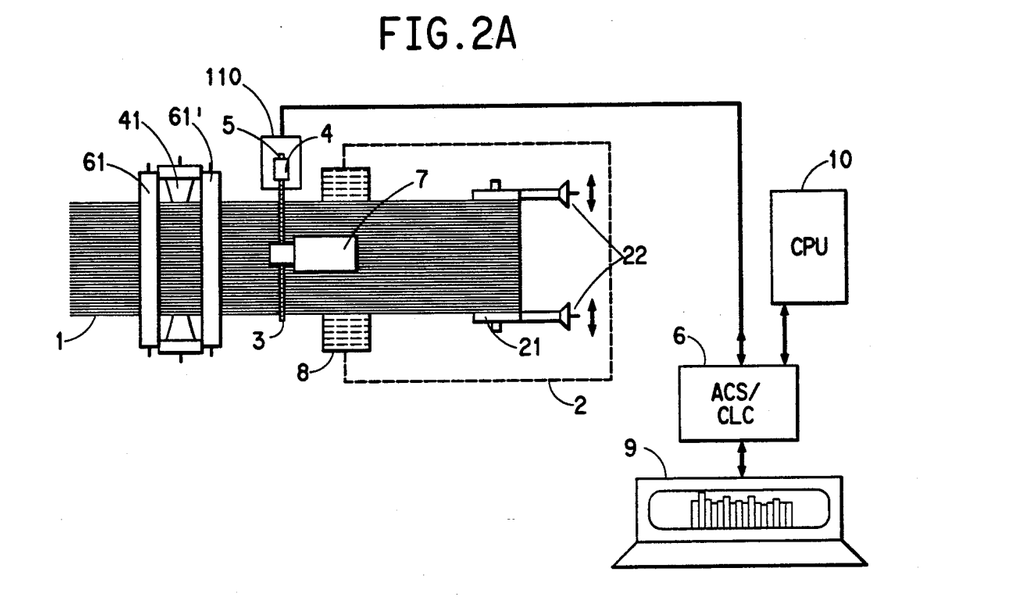
FIGS. 2A and 2B are enlarged plan and elevation views, respectively, of a mass monitoring and tow guiding system of FIGS. 1A and 1B.
Figure 2B:
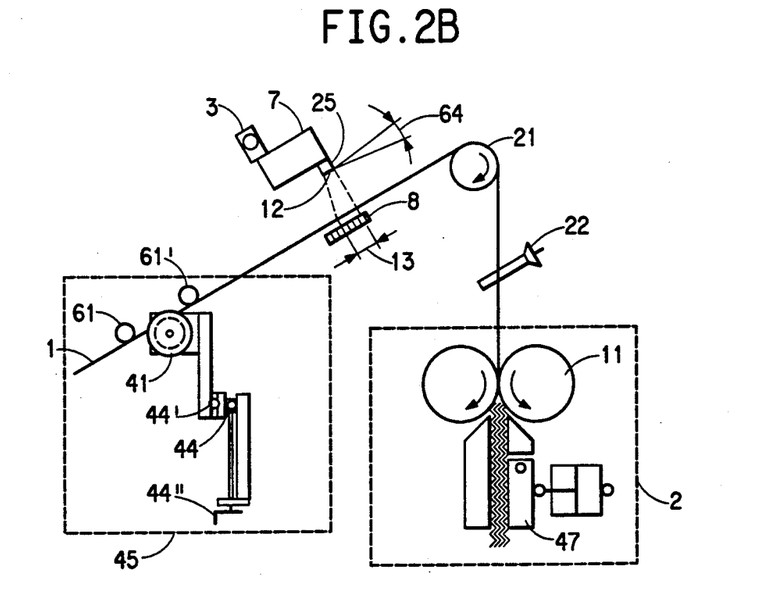
Figure 3A:
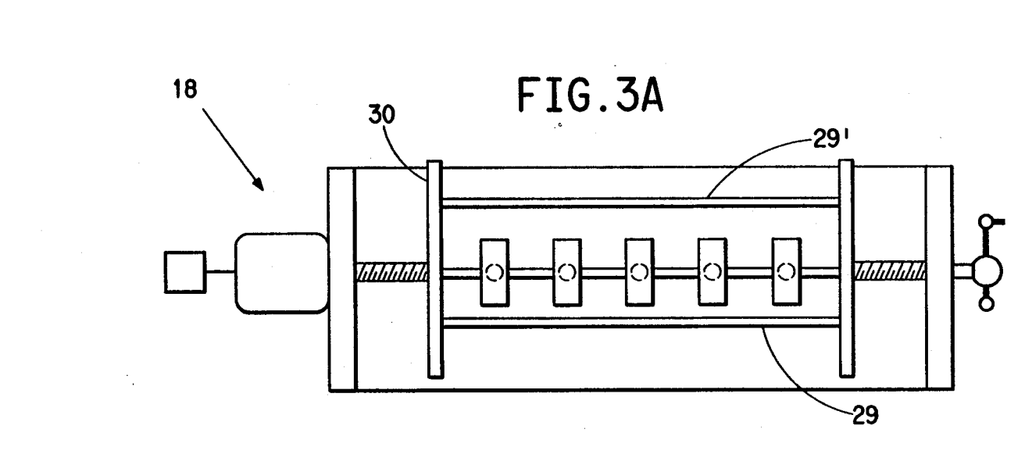
FIGS. 3A, 3B and 3C are plan, elevation and end view, respectively, of a tow guide with manual adjustments for individual tows.
Figure 3B:
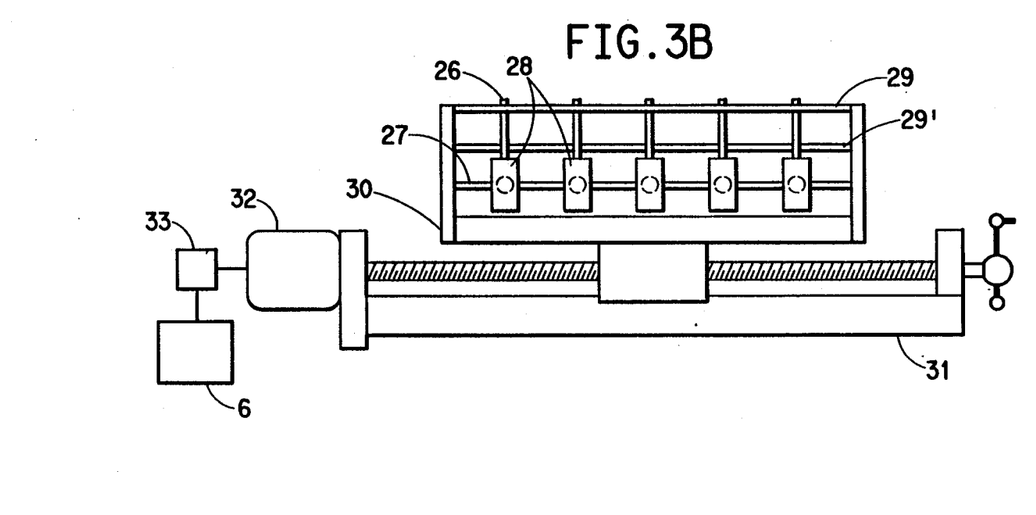
Figure 3C:
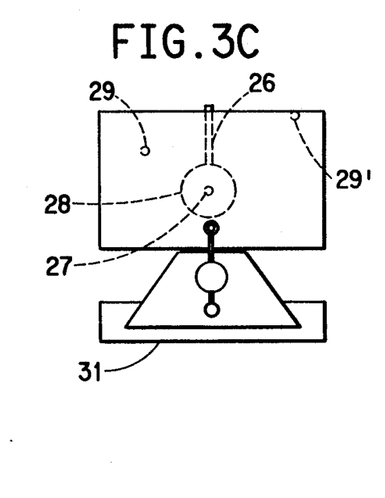
Figure 4A:
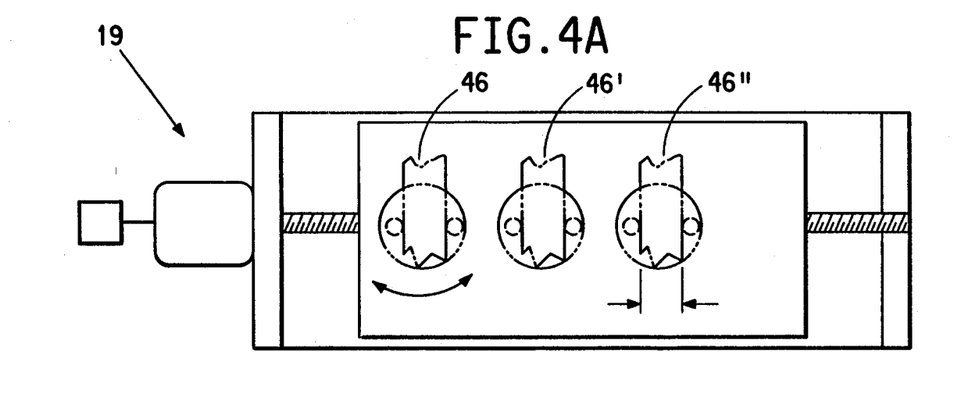
FIGS. 4A and 4B are plan and elevation view, respectively, of a tow guide with automated adjustments for individual tows.
Figure 4B:
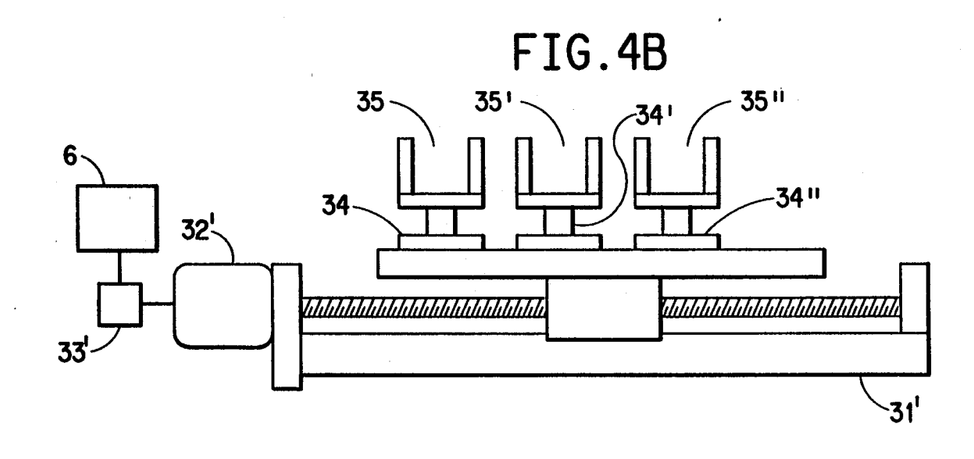
Figure 9A:
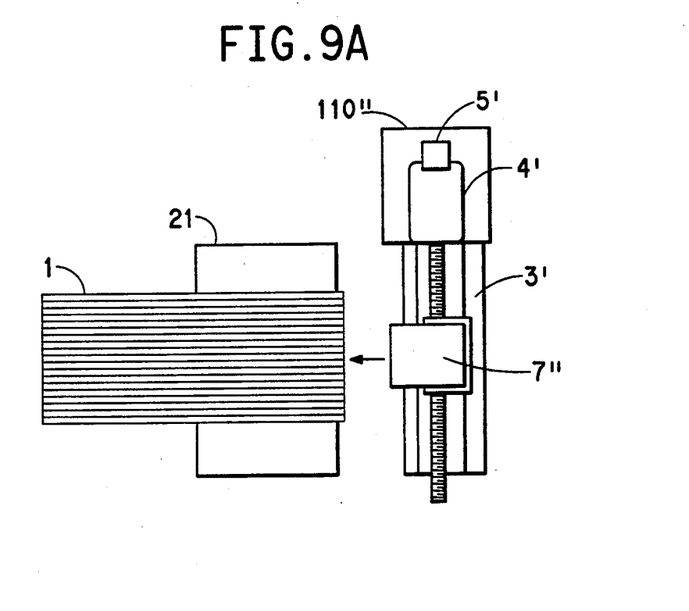
FIGS. 9A and 9B are plan and elevation view, respectively, of a direct contact device for measuring tow band thickness.
Figure 9B:
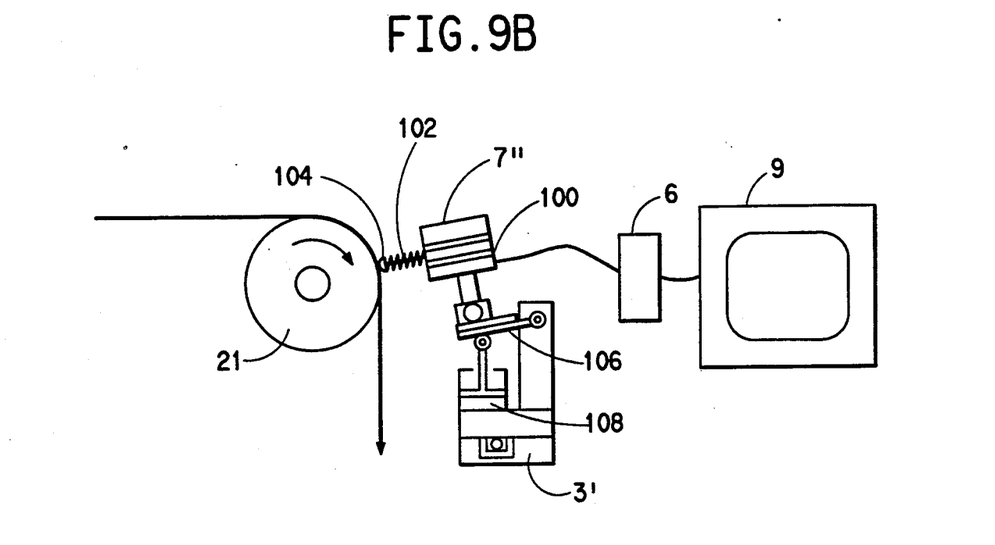

Any of the several devices can be used to accomplish the task of monitoring tow cross section. FIGS. 2A and 2B show a preferred embodiment of a cross-section sensor 7 which consists of a near-infrared, non-contact, mass sensor mounted above a non-contact, reflector, reference plate 8. FIGS. 9A and 9B show another embodiment of a cross-section sensor 7" which consists of a contacting linear voltage differential transducer (LVDT) thickness sensor mounted over a contacting roller 21.

The mass sensor system (FIG. 2) for monitoring the composite tow band 1 as it enters the crimper 2 consists of an indexing traverse mechanism 3, driven by a variable speed motor 4 with an attached shaft encoding device 5 which feeds a signal to the ACS 6 indicating the relative position of the near infrared mass sensor 7 as it moves across the running tow band. The entire motion control device 110 comprises elements 3, 4 and 5.

A ceramic reflector reference plate 8 is located below the tow line to provide a constant reference background and to increase the reflected signal to the mass monitor. The sensor face 12 is set at angle 64 of nominally 10 degrees with respect to the reflector 8 to prevent a first surface reflection and to improve accuracy of the measurement.

Data for desired tow cross sections are entered into the ACS 6 either by a direct operator control station 9 or from a remote central process computer (CPU) 10. Typical data input is the location of the geometric centerline of the crimper rolls 11 and desired cross sectional profile. The primary interest for guiding purposes is the relative thickness or mass of the band, not its actual thickness or mass; therefore, calibration is not essential to operation of the profile monitor.

Non-contacting sensors 7 and 7' (FIG. 1) such as the Microquad model 8000 infrared moisture monitor manufactured by Moisture Systems Corporation, Hopkinton, MA are preferred for this application because it has sufficient resolution for this application and can provide multiple sensor outputs such as mass and moisture. The Micro-Quad 8000 operates by emitting near infrared light beams. It uses two light beams to measure the nylon content and two light beams to measure other content such as water. The first beam, called the reference beam, is not strongly absorbed by the nylon or the background. This is used to determine how much reflected light to expect. The second beam, called the measure beam, is strongly absorbed by the nylon. The Micro-Quad sensor then measures how much of the reference and measured beams are reflected back to the sensor from the material. The ratio of the reflected reference beam divided by the reflected measuring beam is proportional to the amount of nylon present.

Sensing area 13 for the mass monitor (FIG. 2B) must be kept small for precise monitoring to detect local perturbations. The Microquad device used had a 0.20 inch wide lane which proved adequate for this application; however, application of this technology is not limited to this range and both wider and narrower units can be utilized satisfactorily depending on the nature of the adjustment and sensitivity desired for discrete process control.

FIGS. 9A and 9B show a plan and elevation view of a direct contacting thickness sensor which can be used in place of a mass sensor. Sensing the thickness provides the same degree of cross-section profile control as mass as long as the density of the tow is essentially uniform. The thickness sensor consists of an indexing traverse mechanism 3' with sensor 7" attached, driven by a variable speed motor 4' with an attached shaft encoding device 5', all similar to that used with the mass sensor. The encoder sends position signals to the ACS 6. The traversing assembly is positioned adjacent the tow entrained around roll 21. The sensor 7" consists of a LVDT displacement transducer 100 urged toward the tow by spring 102 that holds ceramic button 104 in gentle contact with the tow. The ceramic button has a 60 degree conical tip with a 0.060 inch radius end to provide a narrow sensing area. Spring pressure should not exceed 200 grams to avoid product damage. The roll 21 is precisely aligned with the traversing sensor. The sensor 7" is attached to the traverse mechanism via pivot arm 106 which can be adjusted in two planes to align with roll 21. Cylinder 108 can raise and lower pivot arm 106 to engage and disengage the ceramic sensor button with the tow band. The roll surface serves as a zero reference plane for the sensor. When the sensor first detects the tow, it starts calculations for determining the thickness and centroid of the tow; it stops calculations when it returns to the base reference or zero point on the other side of the tow. A 0 to 24 volt DC signal is sent from the LVDT to a remote computing device. The computing device begins calculations for centroid when a preset threshold voltage is exceeded and ends when the sensor returns below the threshold voltage. A voltage signal is sent from this device to the ACS/CLC (6).

For read time process control of all guiding elements, an Advisory Control System (ACS) or closed loop controller (CLC) 6 (FIG. 7) may be used in conjunction with a series of tow band shape and size sensors. These are digital devices and appropriate signal conditioning units are provided for interface with the remote stepping motors and shaft encoding devices attached to the guides to support precise repeatable adjustment. Only one tow shape sensor is needed to measure and automatically control tow profile. However, two units allow improved precision and allow for control of individual band widths as well as profile. Output data from these sensors 7, 7' and 7" which include edge location and local mass are fed into the ACS/CLC processor 6 and output signals, proportional to centroid, are delivered to a series of remote positioning devices attached to guides located at strategic locations throughout the drawing process (FIGS. 1A, 1B, 2A and 2B) 18, 19, 21, 41, 22 and 40.

A set point for individual guide locations, plus other desired performance data, such as tow profile, is entered into the ACS system 6 from an operator console 9 or from a central process computer 10. Position of individual guiding components is fed back to the ACS/CLC 6 from shaft encoding sensors located at each guide 33 and 33', 44, 44' and 44", 53 and 53' and 60 and 60' (FIGS. 1 and 3-6).

The cross-sectional measuring devices 7, 7' and 7" can either be fixed to monitor portions of the cross section or traversed to monitor the entire band. When traversing, the devices typically scan a 12 inch cross section in 30 seconds. However, they can be operated across a broad range depending on the tow speed. Index rates should be established based on process dynamics to provide a realistic input of actual variability.

A manually adjustable entrance guide 18 (FIGS. 1 and 3A) is used when only one mass detector is in use. This unit moves left and right to position the entire group of tow lines entering a draw line across the face of the draw rolls. This guide consists of a series of adjustable pins 26 which can be manually adjusted and which are mounted on a common shaft 27. A set screw or detent 28 is provided to secure the pin at the desired location. A pair of restraining bars 29 and 29' are provided to keep the moving tow band captive between the pins. The guide bars and pins are mounted in a frame 30 attached to a motorized slide 31 which is driven by motor 32. A shaft encoding device 33 signals the ACS/CLC 6 of the guide's location.

Entrance guide 19 (FIGS. 1 and 4) is used in place of guide 18 when additional mass detector 7' is used and individual band width control is desired in addition to cross section control. This guide moves left or right to center the total mass and individual pins 35, mounted on rotary tables 34, 34' and 34" can be rotated based on a signal from a remote sensor 7' to adjust the width of individual tow bands entering the draw line. This unit is mounted on a motorized slide 31' driven by a motor 32'. Its location is sensed by an encoding device 33' with final control data sent to the ACS/CLC 6. Mass monitor 7 identifies the location of the entire tow and individual band width is detected by sensor 7'.

A commercial post draw stacking guide 40 (FIG. 1) which is capable of stacking individual tow lines on top of each other and positioning the combined group of lines in a specific location for later entry into the crimper, is included for overall position control. Position sensors 60 and 60' provide operator input as to guide position with respect to a home position.

Convergence and shaping guide system 45 (FIGS. 2A and 5A) near the entrance to the crimper is capable of altering the inlet profile to the specific shape needed for optimum side to side crimp uniformity. A preferred profile is a generally flat tow cross section with slightly fat edges in the last 0.100–0.0150 inch to offset the side wall friction of the stuffing box. The shaping guide 41 (FIG. 2) used in conjunction with two flat rollers 61 and 61' is provided as a final trim device to shape and size the band entering the crimper. Guide 41 is mounted in a base 42 which is attached to a motorized two axis adjustable slide and turn table unit 43. Each axis has its own position detection encoding device 44, 44' and 44" which feeds signals to the ACS/CLC unit 6.

Figure 6A:
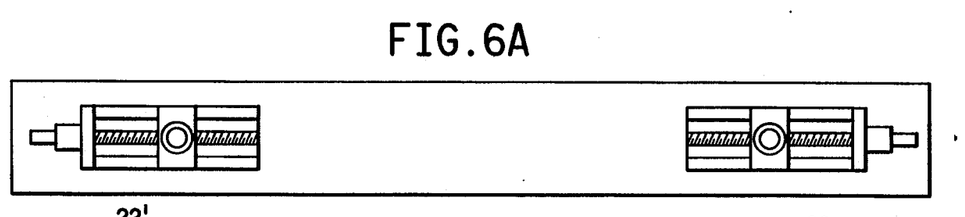
FIGS. 6A and 6B are plan and elevation view, respectively, of a pair of tow edge guides.
Figure 6B:
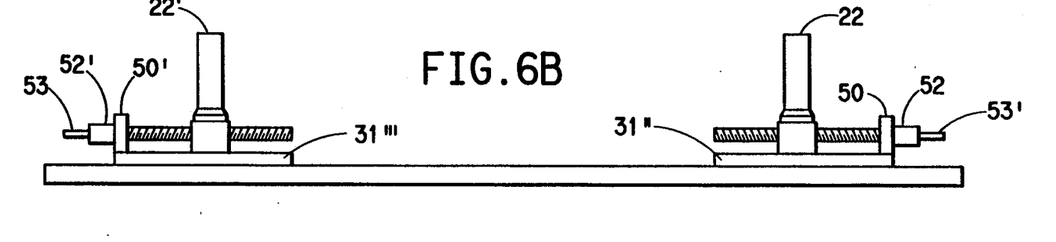

Edge shaping guides 22 and 22' in FIG. 6B are placed on either side of the tow entering the crimper. They consist of a pair of motorized slides 50 and 50' driven by motors 52 and 52' with shaft encoding devices 53 and 53'. These guides are set manually by the operator. Manually adjusted guides can also be used in this operation. However, they are not preferred because they do not allow the operator to see the change on his monitor as cross-sectional scans are made.

| Apparatus Components | | | |
|---|---|---|---|
| Element Nos. | Name | Model No. | Manufacturer or Reference |
| 3 and 3' | Indexing traverse mechanisms | IMC-120 | Aldridge, Inc. Virginia Beach, VA |
| 4 | Motor | IMC-120 | Aldridge, Inc. Virginia Beach, VA |
| 5 | Shaft encoder | IMC-120 | Aldridge, Inc. Virginia Beach, VA |
| 6 | Automatic and closed loop | PLC'3 and 5 | Allen Bradley Corp., Milwaukee, WI |
| 7 and 7' | Mass sensor | Microquad 8000 | Moisture Systems Corp. Hopkinton, MA |
| 8 and 8' | Ceramic reflector Reference plates | None | Generic glazed ceramic tiles - white |
| 9 | Operator control station | T-35 | Allen Bradley, Inc Milwaukee, WI |
| 10 | Central process computer (CPU) | VAX-11-750 | Digital Equipment Corp. Nashua, NH |
| 12 | Non-contacting | Microquad 8000 | Moisture Systems |

-continued

| Apparatus Components | | | |
|---|---|---|---|
| Element Nos. | Name | Model No. | Manufacturer or Reference |
| | sensor 7 face | | Corp. Hopkinton, MA |
| 31 and 31' | Motorized slides | H8-24-8MSB-LS | R. T. Gilman Grafton, WI |
| 32 | Stepping motors | 101SMB2-HM | Aerotech Pittsburgh, PA |
| 33 and 33' | Shaft encoding devices | 1771 QA | Allen Bradley, Inc. Milwaukee, WI |
| 34 | Rotary table | 83 | Palmgren Chicago, Il |
| 40 | Stacking guide | None | Neumag GmbH Neumunster, W. Germany |
| 44, 44' and 44" | Shaft encloding devices | 1771 QA | Allen Bradley, Inc. Milwaukee, WI |
| 50 and 50' | Motorized slides | 12-3-¾-MSB-LS | R. T. Gilman Grafton, WI |
| 52 and 52' | Stepping motors | 101SMB2-HM | Aerotech Pittsburgh, PA |
| 53 and 53' | Shaft encloders | 1771 QA | Allen Bradley, Inc. Milwaukee, WI |
| 60 and 60' | Position sensors | Digital display unit | Electro-Sensors, Inc. Minneapolis, MN |
| 70 | Pivoting rolls stacking guide 40 | 653205, OL-R | Neumag GmbH Neumunster, W. Germany |
| 100 | Linear voltage differential transducer | 3000 | Hewlett-Packard Co. Palo Alta, CA |
| 102 | Spring | LC-045E-2 | Lee Spring Co. Brooklyn, NY |
| 108 | Air cylinder | BFT-042D | Bimba Mfg. Co. Monee, IL |
| 110 | Motion control device | IMC-120 | Aldridge, Inc. Virginia Beach, VA |

Possible logic functions for operation of the automatic system are:

1. Shift the entire cross section left or right to move the dynamic centerline of the running tow line to correspond with a preset geometric centerline using guides 18 or 19.
2. Without changing the centerline of the mass, change the tow profile to meet a predefined profile by moving the individual tows making up part of the lines left or right to alter the cross section using 19.
3. A mixture of 1 and 2.
4. Using the shaping guides system 45 and edge guides 22/22' to change the profile of the band by raising 41 to narrow or lower 41 to widen the band or rolling 41 left or right to alter the side to side shape. Use edge guides 22 and 22' to make minor adjustments to the band as it enters the crimper to offset side wall frictional effects.

Typical examples of control modes follow to illustrate the flexibility of the proposed invention (FIG. 7):

Mode 1

Figure 7:
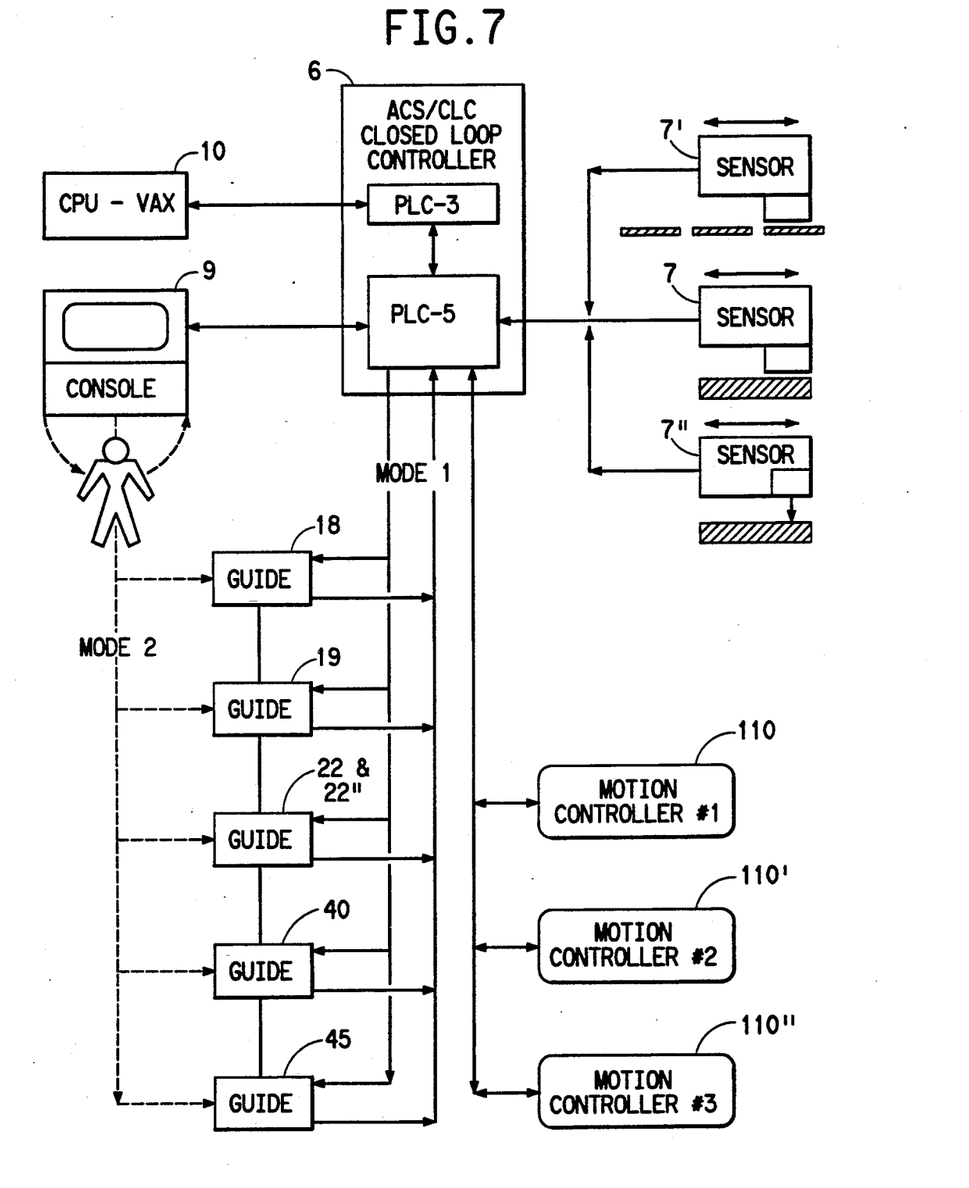
FIG. 7 shows a block diagram of closed loop control system for controlling tow mass distribution.

Automatic movement of guides by ACS/CLC based on preprogrammed logic instructions from a current location to a new set point location based on an encoded measurement indicating a deviation from a predetermined set point. The use of encoding devices to sense guide positions is preferred but other sensors such as LVDTs may be used.

The sequence of events for automatic guiding consists of:

1. Monitoring the cross-sectional mass of the moving tow band at a predetermined frequency.
2. Calculation of the mass centroid using equations in the central process unit 6.
3. Comparison of actual mass profile and centroid with predetermined standard stored in the central process unit 6 or remote computer 10.
4. Determination of required action by ACS 6 if measured profile does not correspond to goal shape per pre-established action elements in the ACS 6.
5. ACS or closed loop controller 6 sends signals to remote guides to move a fixed distance to offset measured error.
6. Feedback by guide sensors as to new position after action completed.
7. Rescanning of tow mass by sensor 7, 7' or 7" to confirm adequacy of adjustment, and additional action if error not totally resolved by first adjustment.
8. Notification of action to operator and recording in remote computer of upset period for possible later removal of off standard crimped product.

Mode 2

From a visual cross-sectional display to the operator from a CRT, display panel, or typewriter, a manual signal is sent to ACS/CLC from the operator control station to relocate the guide(s) to a new location, or at his option the operator can physically adjust the guide(s).

An example of the guiding sequence for an integrated draw line containing several guiding elements is as follows:

From mass sensor 7, 7' or 7" the centroid for a given mass profile is calculated to establish the dynamic centerline of the running tow line. The calculated centerline position is compared versus a desired centerline preset by the operator from console 9 or input from the process computer 10. If the deviation detected is greater than some acceptance dead band, a set point for one of the ACS guides is determined and instructions to the device are sent to move to a new location.

The centroid is calculated using well established procedures for determination of the centroid of an area as defined in "Vector Mechanics for Engineers (Statistics and Dynamics)" by F. P. Beers and E. R. Johnston, Jr.

If the instructions require the selected guiding element to move beyond a predetermined maximum, two commands would be issued and coordinated to move a pair of guide units to center the range of each component. Updates are sent after each traverse of the sensors 7, 7' or 7" until the system is stabilized. If corrective action necessary for any guide exceeds its capabilities, the operator is automatically notified of the condition.

Figure 12:
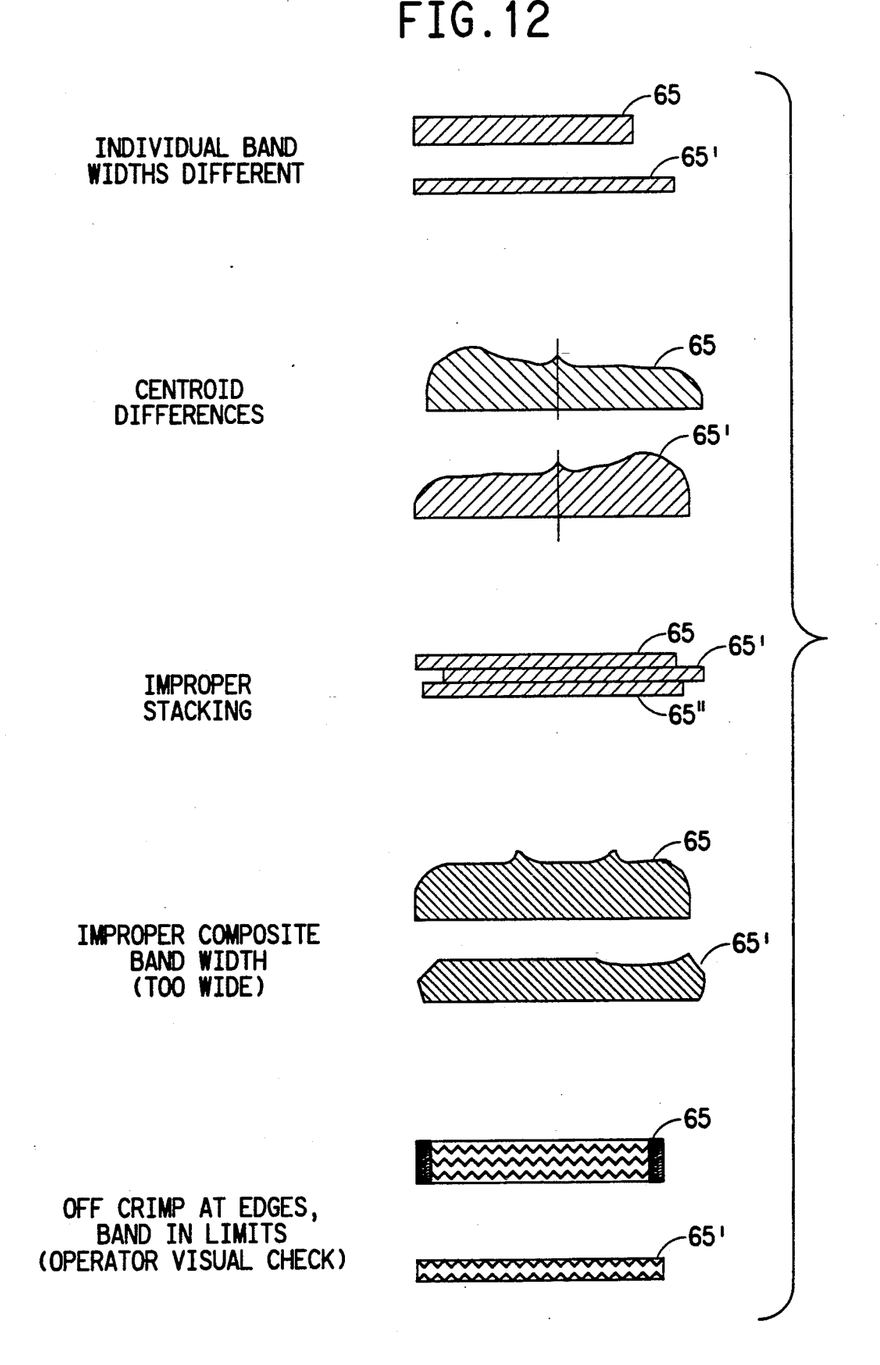
FIG. 12 illustrates some of the cross-section conditions correctable by means of the invention.

The following lists some cross-sectional conditions illustrated in FIG. 12 that can be controlled with the system of the invention:

| CROSS-SECTION CONDITION | ADJUSTMENT |
|---|---|
| 1. Individual Band width difference | Manually adjust pin spacing 26 on guide 18, or Automatically adjust pin spacing 46 and 46" on guide 19 |
| 2. Centroid differences | Move 18 or 19 left or right to center mass, |

| CROSS-SECTION CONDITION | ADJUSTMENT |
| --- | --- |
| 3. Improper stacking | Roll 41 right or left to shape band, and adjust horizontal position of 41 to stay on centerline of crimper with 44<br>Position 18 or 19 on crimper centerline to center midline, or Manually move stacked band 65 and 65" left, Adjust individual band wide line 65' and 65" by rotating 35, 35' and 35". |
| 4. Improper composite band width (too wide) | Narrow band by raising 41 with 44". |
| 5. Off crimp at edges, band in limits (operator visual check) | Adjust edge guides 22 and 22' via motors 52 and 52', Alter band width as needed by raising or lowering 41. |

ADJUSTMENT MANUAL SEQUENCE

Startup

Entrance guide 19 is positioned to feed the tow bundles about the geometric centerline of the crimper.

Entrance guide (FIG. 4B) pins 35 through 35" spacings 46 through 46" are set to obtain the desired individual line widths. Tow widths vary depending on the number of lines fed into the system and number of lines to be stacked.

Stacking guide (FIG. 6) 40 is set to position each ribbon of equal size on top of each other.

Figure 5A:
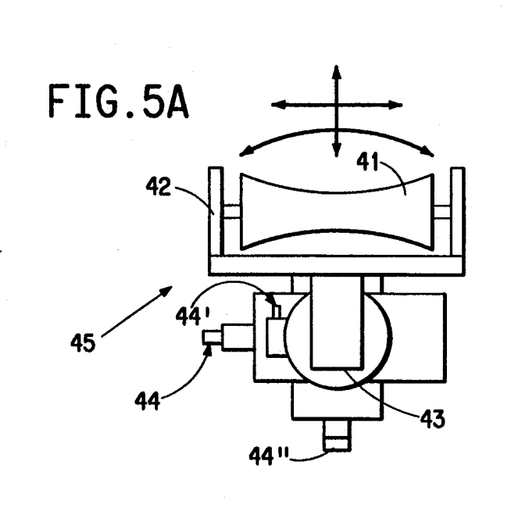
FIGS. 5A and 5B are elevation and end view, respectively, of a tow width guide.
Figure 5B:
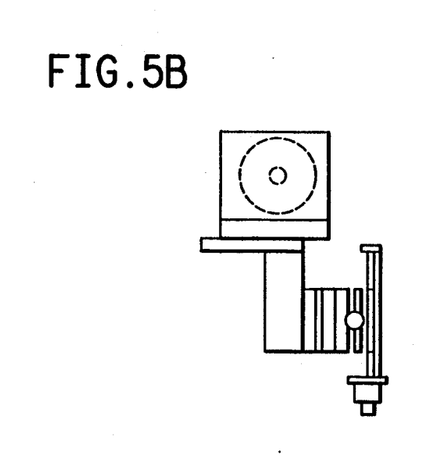

Rolling convergence guide 41 (FIG. 5) is set as follows:

Elevation function 44" is adjusted to feed a ribbon 0.125–0.0200 inch wider than the crimper roll width.

Horizontal position function 44 is set on the crimper roll geometric centerline.

Angular position function 44' is set at zero degree. (Note: crimper 2 must be precision aligned to adjacent guiding rolls at installation.)

Shaping guides 22 and 22' are set to 0.125–0.200 inch less than the crimper roll width to prevent rubbing of edge filaments against the side wall of the stuffing box. Compression of the tow at the nip rolls of the crimper causes the tow to flatten out to an even ribbon. Rolls 22 and 22' are set equal distance from the centerline of the crimper rolls. After preliminary positioning the composite tow to an approximate width and profile, the line is ready for startup.

DYNAMIC OPERATION

Differences in equipment and product properties as tows are processed causing tracking errors which create variations in tow band profile which in turn results in crimp variation.

Migration of the tow lines due to tracking error is usually over a long period of up to several minutes and, therefore, gradual changes in guiding are needed to retain optimum across band profile control. To offset these tracking errors and to provide more precise profile control, guide 45 is used for trim control. Operation of the integrated guiding system is based on the following relationships for adjustment:

Raise roll 41 to narrow the band.

Lower roll 41 to widen the band.

Rotate roll 41 about its centerline to alter cross-section.

Because the guiding system 45 is not on the centerline of the moving tow line, X-Y adjustment is needed to retain the centerline adjustment whenever the guide is rolled left or right. An algorithm is provided in the ACS to maintain the relationship; functions 44, 44' and 44" are used for these corrections.

AUTOMATIC SEQUENCE

Figure 8A:
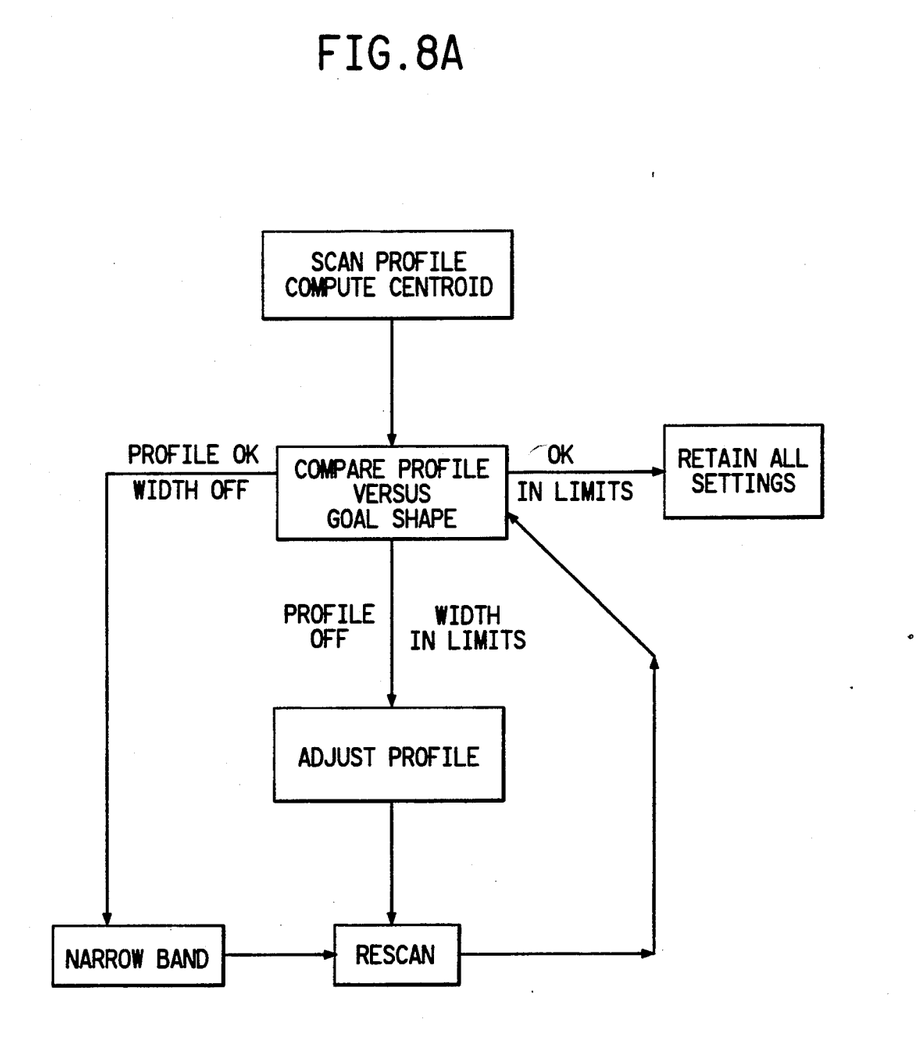
FIGS. 8A and 8B are block flow diagrams describing the control logic for controlling tow guides at two different positions in a tow processing line.
Figure 8B:
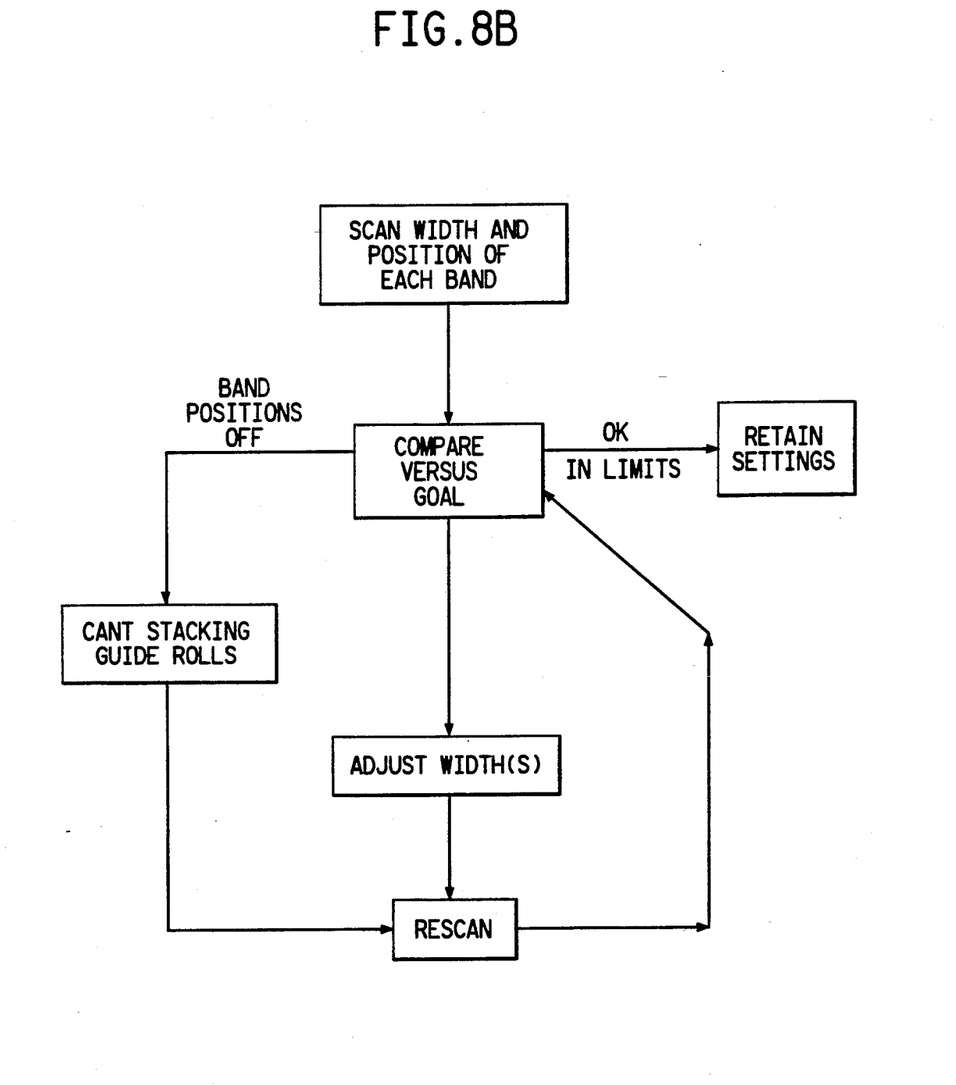

Logic sequence (FIGS. 8A and 8B) for automatic control is provided to identify control elements and order of guiding adjustments. Operation in automatic mode can start by using data from the previous shutdown position or from the manual startup centerline reference point. The machine operator selects the desired mode of operation prior to starting the draw line and in the case of fully automatic sequencing the following operations would occur:

The line runs at jog speed of 50 to 75 ypm until a full cycle of the shape and position monitors are completed, about 30 seconds.

If the tow elements and composite band are within the preset limits, the line goes to full speed operation of 200–700 ypm.

If outside the limits, the ACS/CLC 6 computes a new position for each guide element based on the error identified and it sends a signal to move the guides. Shaft encoding devices provide information so the ACS knows when the proper position is reached.

The monitoring devices 7, 7' or 7" are scanning during the reposition operation and recomputations are constantly updated every 30 seconds until the line is within limits.

During normal operation the tow band shape is continuously scanned and guiding updates are performed as needed. Any out of limits production is recorded in the ACS and the machine operator is notified of upsets.

Figure 10:
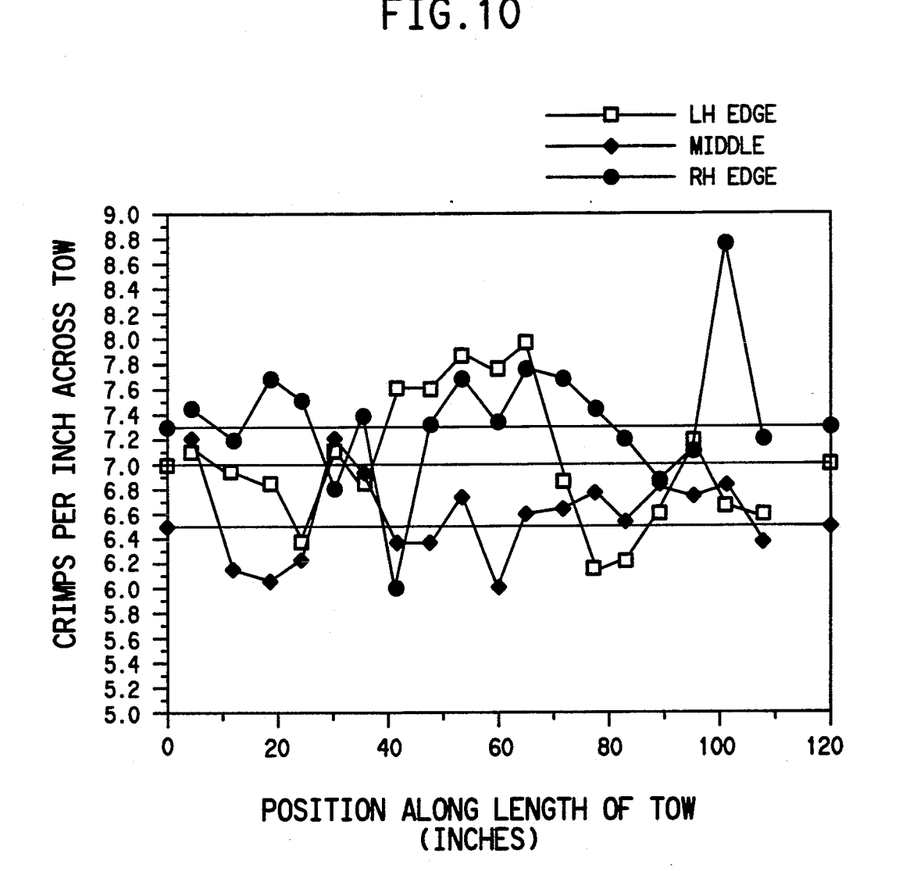
FIG. 10 is a graphical representation of the crimp variations across and along a tow band that was crimped after setting up the guides based on visual monitoring of the tow by an operator without benefit of the system of the invention.
Figure 11:
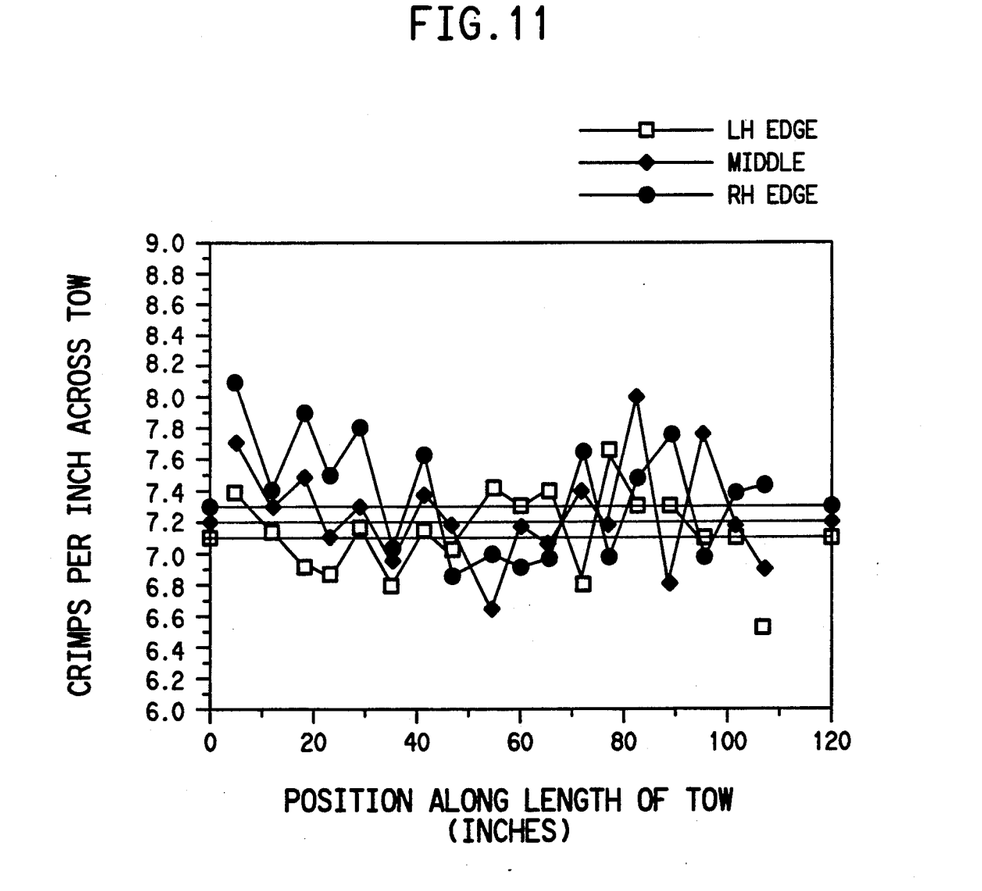
FIG. 11 is a graphical representation of the crimp variations across and along a tow band that was crimped after setting up the tow guides using the thickness measuring system of the invention.

Variations in crimp, as determined by manual measurement of crimps per inch (CPI), across and along the tow band show that transverse crimp control can be substantially improved by use of this system. More particularly, FIG. 11 shows the results of monitoring a tow band profile by use of the thickness monitor of FIGS. 9A and 9B and manually adjusting the guides accordingly before collecting the sample for data analysis. Notice that the standard deviation for the edges has improved considerably compared to the sample of FIG. 10 taken using conventional guiding techniques under the same operating conditions. The mean CPIs for the left, middle and right vary only from 7.13 to 7.21 to 7.34, respectively, which is more uniform that the variations in FIG. 10. At a length along the sample, say 18", the middle CPI is about 7.4, the left is about 6.8 and the right is about 7.8 for a range of variation of 0.9 compared to 1.6 at 18 inches for FIG. 10, an improvement in cross section uniformity.

Along-end-variations are due to changes in applied crimping force which occur as the stuffer box gate 47 moves in response to crimped product flow through the crimper. Improved side to side crimp control achieved through improved guiding reduces the amplitude of this motion, thereby improving the overall crimp uniformity both across and along the tow band; it also improves stability of the crimping process.

What is claimed is:

1. A method for controlling a mass distribution profile of a tow band width of a moving tow band at a predetermined value, said method comprising: sensing the mass distribution profile of the tow band across the width of the moving tow band; comparing the sensed mass distribution profile to a predetermined value of the mass distribution profile and determining the difference between the sensed and predetermined mass distribution profile; generating a signal proportional to said difference; and moving at least one positioning device in accordance to said signal to adjust a position of the tow band and thereby adjust said mass distribution profile toward the predetermined mass distribution profile.

2. An apparatus for controlling a mass distribution profile of a moving tow band width, said apparatus comprising: means for sensing the mass distribution profile of the tow band across the width of the tow band; means for comparing the sensed mass distribution profile to a predetermined mass distribution profile and generating a signal proportional to the difference between the sensed and predetermined mass distribution profiles; and positioning means movable in accordance to said signal for adjusting a position of said tow band so as to adjust the mass distribution profile toward the predetermined mass distribution profile.

* * * * *